United States Patent
Rees

Patent Number: 6,034,760
Date of Patent: Mar. 7, 2000

[54] METHOD OF DETECTING WEATHER CONDITIONS IN THE ATMOSPHERE

[75] Inventor: Frank L. Rees, Baltimore, Md.

[73] Assignee: Flight Safety Technologies, Inc., New London, Conn.

[21] Appl. No.: 08/955,282

[22] Filed: Oct. 21, 1997

[51] Int. Cl.[7] .............................. G01P 3/36; G01N 21/00; H04R 1/02
[52] U.S. Cl. ......................... 356/28.5; 356/342; 367/149
[58] Field of Search ................................... 356/4.01, 28.5, 356/342; 367/149

[56] References Cited

U.S. PATENT DOCUMENTS

| | | |
|---|---|---|
| 3,540,829 | 11/1970 | Collinson et al. . |
| 3,665,467 | 5/1972 | Haroules et al. . |
| 3,693,015 | 9/1972 | Funk, Jr. . |
| 3,723,004 | 3/1973 | Brayton . |
| 3,738,750 | 6/1973 | Kalb et al. . |
| 3,800,906 | 4/1974 | Albares . |
| 3,825,341 | 7/1974 | Goto . |
| 3,968,362 | 7/1976 | Mocker . |
| 3,984,685 | 10/1976 | Fletcher et al. . |
| 4,167,329 | 9/1979 | Jelalian et al. . |
| 4,168,906 | 9/1979 | Schwiesow . |
| 4,195,931 | 4/1980 | Hara . |
| 4,303,862 | 12/1981 | Geiger . |
| 4,351,188 | 9/1982 | Fukushima et al. . |
| 4,359,640 | 11/1982 | Geiger ..................................... 356/342 |
| 4,397,549 | 8/1983 | Morgan . |
| 4,465,372 | 8/1984 | Geary . |
| 4,483,614 | 11/1984 | Rogers .................................. 356/28.5 |
| 4,506,979 | 3/1985 | Rogers . |
| 4,585,341 | 4/1986 | Woodfield . |
| 4,589,070 | 5/1986 | Kyrazis . |
| 4,630,051 | 12/1986 | Adams et al. . |
| 4,652,122 | 3/1987 | Zincone et al. . |
| 4,715,707 | 12/1987 | Reynolds et al. . |
| 4,735,503 | 4/1988 | Werner et al. ......................... 356/28.5 |
| 4,779,222 | 10/1988 | Harrison et al. . |
| 4,838,687 | 6/1989 | Pfeifer . |
| 4,875,923 | 10/1989 | Rogers et al. . |
| 4,893,923 | 1/1990 | Javan . |
| 4,996,473 | 2/1991 | Markson et al. . |
| 5,007,731 | 4/1991 | Butefisch . |
| 5,088,815 | 2/1992 | Garnier et al. . |
| 5,214,484 | 5/1993 | de Mollerat du Jeu . |
| 5,216,478 | 6/1993 | Kadowaki et al. . |
| 5,221,927 | 6/1993 | Palmer .................................. 356/28.5 |
| 5,379,270 | 1/1995 | Connolly . |
| 5,394,238 | 2/1995 | Mocker et al. . |
| 5,469,169 | 11/1995 | Frush . |
| 5,504,577 | 4/1996 | Lonnqvist et al. . |
| 5,504,719 | 4/1996 | Jacobs . |
| 5,523,759 | 6/1996 | Gillberg et al. . |
| 5,587,785 | 12/1996 | Kato et al. . |

OTHER PUBLICATIONS

"Infrasound Originating Near Mountainous Regions in Colorado", A.J. Bedard, Jr., Journal of Applied Meteorology. vol. 17, No. 7, Jul. 1978.

Primary Examiner—Stephen C. Buczinski
Attorney, Agent, or Firm—David A. Tamburro

[57] ABSTRACT

Method and apparatus for detecting conditions in the atmosphere which are hazardous to flying aircraft and providing early warning to pilots or ground personnel. The method includes using a laser beam and a coherent optical receiver to optically sense sound waves produced by those hazardous conditions and measuring the effect of those sound waves on the transmitted and received optical beams.

33 Claims, 5 Drawing Sheets

METHOD OF DETECTING WEATHER CONDITIONS IN THE ATMOSPHERE

BACKGROUND OF THE INVENTION

This invention relates generally to a sensing system for detecting adverse weather conditions which are hazardous to flying aircraft and more particularly to a sensor for optically characterizing ring-eddy atmospheric turbulence emanating sound (SOCRATES) produced by aviation hazards such as clear air turbulence, windshears, microbursts, and aircraft generated wake vortices, all of which at some time or another have proved to be hazardous to aircraft and its passengers. The information gathered by the system provides early warning to pilots or ground based personnel.

In the past various proposals have been offered to provide information regarding hazardous weather conditions to airborne pilots or to ground based personnel and some of those proposals have included laser detection devices which sense such atmospheric conditions as temperature, water vapor content, and air velocity as indicators of weather conditions. None of these prior laser based systems has been widely accepted commercially.

Other types of detection systems such as weather-SODAR (Sound Detection and Ranging) and weather-radar have been used but these systems do not provide an all weather capability because they measure weather conditions in such a way that they experience reduced energy backscattering under the very turbulent mixing of air masses they are trying to detect. Consequently these systems have a tendency to fade away during bad weather conditions at a time when they are needed most. Similarly, weather lidar systems, although more accurate than weather radar, are known to be less weather tolerant than their radar counterpart.

Consequently there is a need for greater airline safety due to recent aviation catastrophes or near disasters whose causes remain unexplained or attributable to clear air turbulence, wake vortices, windshears, and microbursts.

Since about the 1970's, it has been recognized that these atmospheric phenomena contain or generate acoustic patterns or signatures in the form of very low frequency sound waves which travel over long distances relatively unimpeded by the surrounding weather or other atmospheric phenomena. This sound generation phenomena, known as ring-eddy vortexing and its associated velocity circulation and unsteady flow fields, essentially create radiated sound which resembles the wave patterns occurring in a body of water after a pebble has been tossed into it. The rings created by the pebble intrusion are similar in shape to the acoustic patterns associated with severe thunderstorms, wake vortices and other clear air turbulence.

It has also been publicly known since about the 1970's that moving objects such as ships, submarines or animals in water generate and radiate sound waves which may be detected by a laser sensing system utilizing free space or wave guided light beams to indicate the presence and location of those sound radiating or reflecting objects in the water. One such system is illustrated in Jacobs U.S. Pat. No. 5,504,719.

However, despite this prior public knowledge, no one has suggested or successfully implemented a laser detection system responsive to sound waves produced by adverse and hazardous weather or wake-vortex conditions to provide an advance warning of those conditions to aircraft pilots or airport ground personnel.

The SOCRATES system of the invention is intended to do just that.

SUMMARY OF THE INVENTION

Accordingly the primary object of this invention is to provide novel method and apparatus for detecting adverse weather conditions in the atmosphere which pose a hazard to flying aircraft.

Another object of the invention is to provide a novel method for detecting adverse weather conditions in the atmosphere such as clear air turbulence, wind shears as well as the severe wind gusting along a mountainous approach to an airstrip, microbursts, and/or wake vortices or tornados or even engine noise of approaching aircraft or friendly or terrorist fired missiles by optically sensing sound waves produced respectively by those adverse weather or other conditions and thereafter providing early warning signals to aircraft pilots and/or ground personnel.

A further object of the invention is to provide a novel method which uses one or more laser beams to detect sonic waves produced by adverse weather conditions in the atmosphere and thereby afford sufficient time for a pilot and/or ground personnel to take corrective action so that the aircraft may avoid the hazardous weather conditions.

Still another object of the invention is to provide the above novel method which directs optical beams into probe volumes of the atmosphere containing light reflecting matter such as particulates, aerosols and dust that move in response to the sound waves, with the adverse weather or wake-vortex conditions being present in a region of the atmosphere which is spaced a substantial stand-off distance from these probe volumes. As a result the novel system of the invention provides a sufficient period of time for a pilot or ground personnel to take corrective action to avoid the hazardous flying conditions.

An additional object of the invention is to provide novel method with an alternative mode of operation which directs optical beams at full or partial optical reflectors which efficiently return light along optical paths whose speed of light is altered by the arrival of sound waves emanating from adverse weather or wake vortex conditions present in the region of the atmosphere which is spaced a substantial standoff distance from those optical beams. The varying speed of light along each optical path relative to light in a vacuum relates directly to optical refractive index changes as opposed to particle motion changes. In applications where it is not feasible to mount physical retroreflectors to reflect light energy, a combination of particles that reflect light energy and vary it through their motion in concert with refractive index changes cooperate to contribute distinctly different information regarding arrival of sound from distant adverse or wake vortex conditions, but provide their respective maximum responses along axes respectively aligned with or at right angles to a direction common to or bisecting the outgoing and returning light beams.

The above objects of the invention are achieved using light beams propagative in free space except when they encounter particles in motion and/or interact with pressure induced refractive index changes from sound emitted by the described adverse weather or wake vortex conditions being present in a region of the atmosphere which is spaced a substantial standoff distance from the local optically defined regions intercepting the sound waves. The above objects may also be achieved using light waves guided in optical fibers that also undergo path length and speed of light changes respectively equivalent to and replacing particle motion and refractive index variations experienced when local optically defined regions through which free space light waves pass and are intercepted by sound waves emanating from distant adverse weather and wake vortex generated sound sources.

A further object of the invention is to provide novel, laser detection systems as described above which may be mounted directly on an aircraft to provide information directly to the pilot or on the ground adjacent an aircraft runway or around the periphery of an airport in order to provide information to ground personnel directing the approach and landing or take-off and climb to altitude by an aircraft or series of aircraft.

Other objects and advantages will become apparent from reading the following detailed description of the invention wherein reference is made to the accompanying drawings.

BRIEF DESCRIPTION OF THE INVENTION

Figure 1:
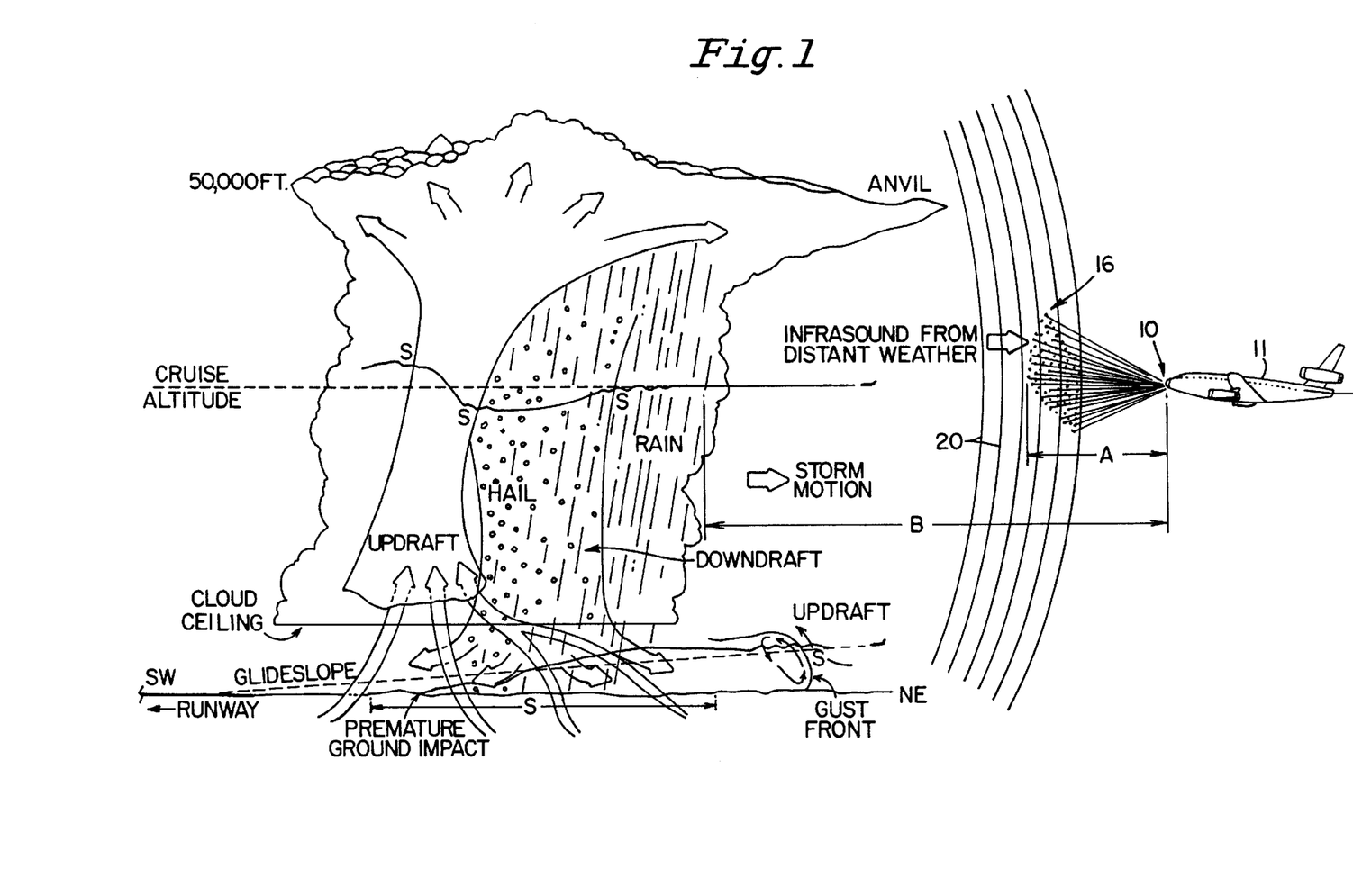
FIG. 1 is a schematic illustration of the laser system of the invention mounted on a flying aircraft for detecting sound waves generated by distant adverse weather conditions in the atmosphere; a similar simplified system may be mounted on the ground.
Figure 2:
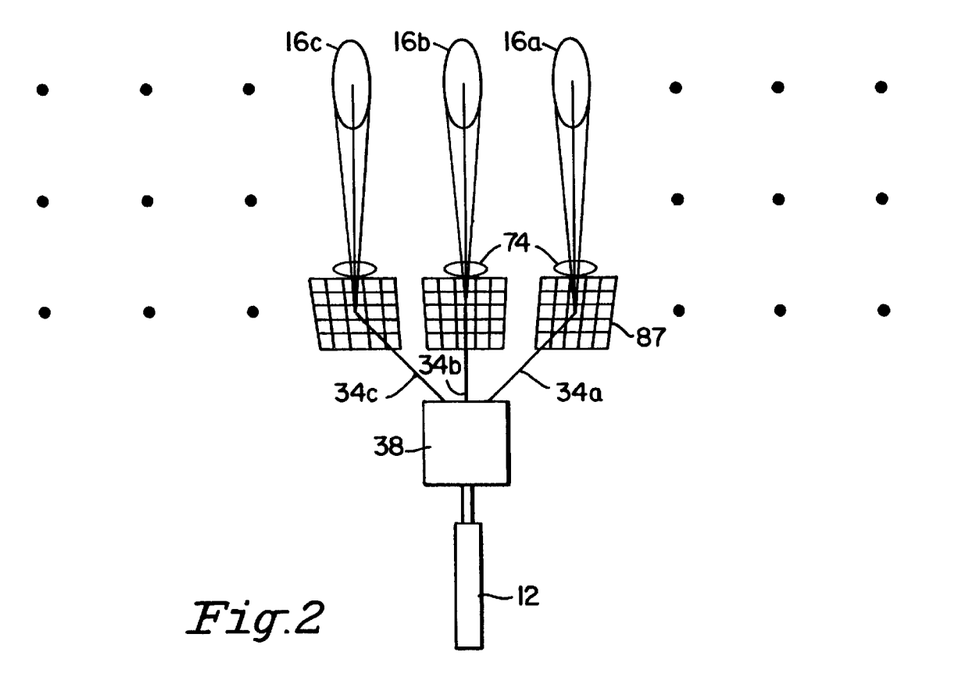
FIG. 2 is a plan schematic illustration of the system of the invention of FIG. 1 employing an array of light beams acting on associated probe volumes in the atmosphere and detecting particle motion within the probe volumes resulting from sound waves generated by distant adverse weather conditions.
Figure 3:
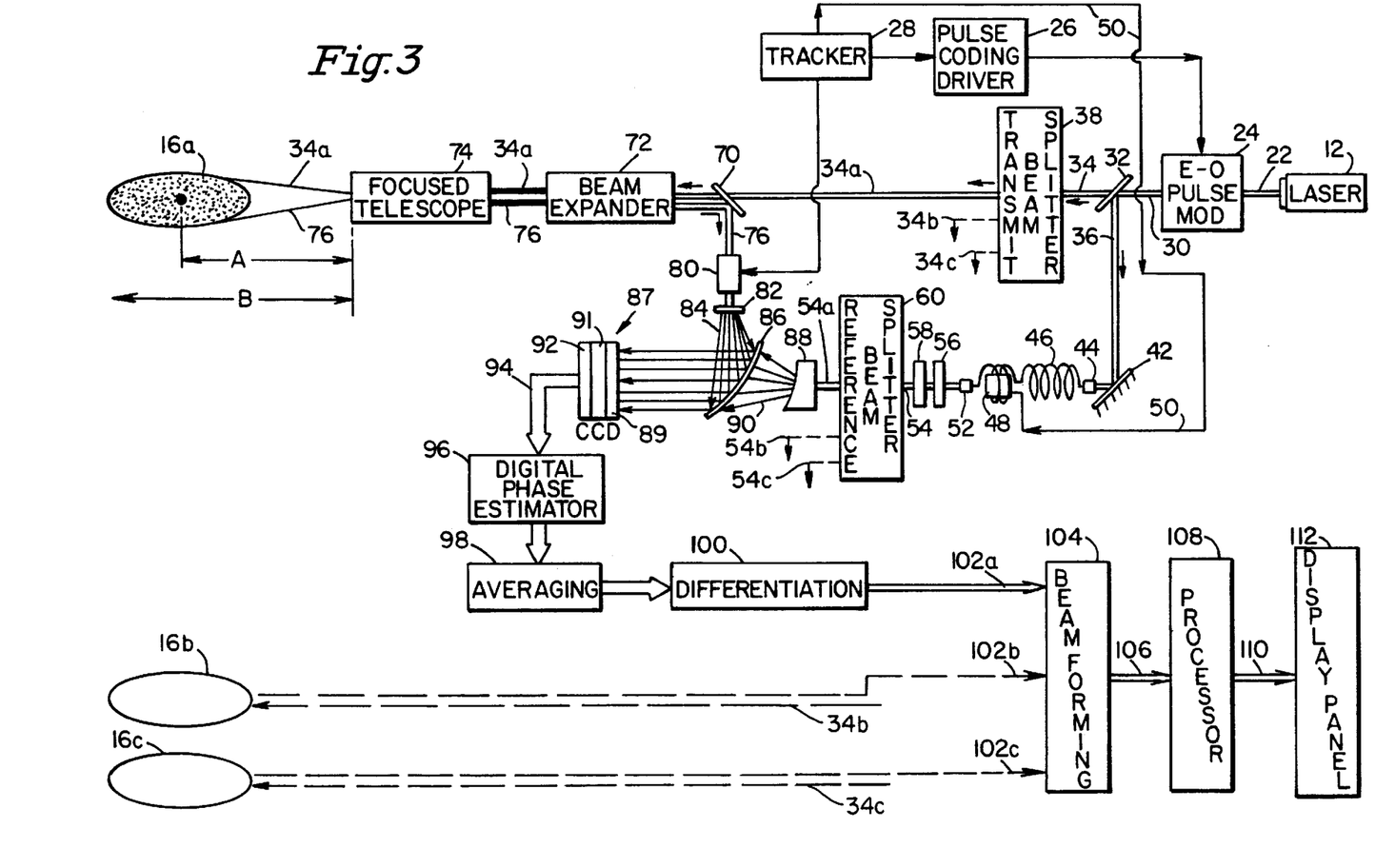
FIG. 3 is a block diagram generally illustrating optical/electrical components associated with each probe volume and forming a part of the array of FIG. 2.

Referring to FIGS. 1–3, the novel laser detection system 10 is mounted on the front of an aircraft 11 and includes a laser 12, a beam splitter 38 adapted to provide a plurality of transmit beams 34a, 34b, 34c, etc. through telescopes 74 to an array of focal or probe volumes 16a, 16b, 16c, etc. located within the atmosphere at a remote sensing range A, e.g. 0.5 km or less, from telescopes 74. The number of beams 34 and probe volumes 16 may vary but preferably there are 128 probe volumes arranged in a three dimensional diverging conical configuration in front of aircraft 11, with the probe volumes acting as virtual microphones to detect infrasound waves 20 generated by hazardous weather conditions present in the atmosphere at a stand-off distance B, e.g. 100 km, ahead of aircraft 11. An acoustic array of virtual microphones covering, for example, up to a two steradian spherical cap centered directly ahead of an aircraft for an airborne system or of a ground base system is suggested. In order to reject backlobe responses from the direction of the aircraft or from behind a ground based system, range displaced probe volumes would be formed to comprise a similar spherical cap array of virtual microphones spaced behind the forward array at about one quarter of an acoustic wavelength, for which such an aperture is designed. Such a bispherical cap array may be designed to accommodate "nested" subapeatures populated with virtual microphone intersticial spacings appropriate to different acoustic frequency sub bands.

The backscattered modulated return beams reflected off the moving particles within the probe volumes are collected by a multichannel receiver based upon a charge coupling device (CCD) 87 that has been adapted for coherent optical mixing and are then processed to provide an early warning to the pilot so that corrective action may be taken if necessary. In that the weather related sound is emitted and received by the virtual microphones almost continously, its travel time is inconsequential because sound packages emitted a couple minutes earlier are heard instanteously. For example, even though the sound waves 20 are travelling at Mach 1, thereby having taken 5 minutes for the sound to reach a stand-off distance of 102 km which prevailed at the time of reception, the pilot of an aircraft traveling at, say, a Mach 0.5 air speed will have been provided with about a further 10 minutes of early warning time. This comes about because such an aircraft will have closed 51 km of the original 153 km distance of the aircraft before receiving the sound that emanated from this original distance from a dangerously swirling air mass, and will take another 10 minutes before encountering it while continuing to travel at Mach 0.5. This 10 minutes is deemed more than sufficient time to take corrective action, and suggests that these sound emanation and reception distances might be halved or more before reaching a critical early warning situation.

Referring now to FIG. 3, the system 10 from FIG. 1 can be identified as a sensor for optically characterizing ring-eddy atmospheric turbulence emanating sound (SOCRATES). It includes a cavity dumped solid state laser 12 operating at about 1.57 $\mu$m or 2 $\mu$m and producing a light beam 22 acted on by an electro-optical (E-O) pulse modulator 24. Modulator 24 is controlled by a pulse coding E-O driver 26, the transmit timing of which is controlled by a platform motion (advection/convection) longitudinal time spacing tracker device 28. The pulsed light beam 30 from modulator 24 is directed to a partially reflecting mirror beam splitter 32 which produces a transmit beam 34 and reference beam 36. Beam splitter 38 then splits beam 34 into a plurality of transmit beams 34a, 34b, 34c, etc. corresponding in number to the number of probe volumes 16a, 16b, 16c, etc, being sensed.

Reference beam 36 is reflected by mirror 42 into a path length matching assembly including a light to fiber optic coupler 44, a fiber optic bulk time delay coil 46, a piezo-electric fiber-optic path length "stretched" delay device 48 which responds to an electronic feedback signal 50 from tracker 28, and a fiber optic to light coupler 52 which emits a matched reference optical beam 54 to a pair of Bragg-cell up/down frequency shifters 56,58 which offset the frequency of the reference beam for subsequent heterodyne mixing with the return beams from the probe volumes. Although not illustrated an outer control loop will be provided by taking the demodulated phase rate output signal 102a (to be later described) and passing that signal to an outer loop averaging filter and a frequency synthesizer. The synthesizer will provide a choice from discrete frequency tonals that are close spaced in frequency and precisely synchronized to a clock frequency involved in controlling surface acoustic wave modulation of the offsetting frequency of one of the Bragg cells up/down frequency shifters 56, 58. After variable gain amplification and then power amplification the so controlled and amplified frequency synthesized tonal chosen to be closest to the mean of the instantaneous Doppler, as represented by averaging a voltage proportional to the phase-rate output signal 102a, is fed back to close an outer mean-Doppler compensation feedback loop. A plurality of this mean-Doppler compensation feedback loop is similarly applied to each of the phase rate output signals 102b, 102c, etc. from the other probe volumes.

The reference beam 54 then passes to a beam splitter 60 which splits the beam into a plurality of reference beams 54a, 54b, 54c, etc, corresponding in number to the number of transmit beams 34a, 34b, etc,. and the number of probe volumes 16.

The optical path for transmit beam 34a, reference beam 54a, and probe volume 16a, and associated optical processing components are illustrated in FIG. 3. Identical optical paths and circuitry (not shown) are provided for probe volumes 16b, 16c, etc., transmit beams 34b, 34c, etc, and reference beams 54b, 54c, etc.

From splitter 38 beam 34a passes entirely through a backside beam deflector 70, beam expander 72, and focused telescope 74 into probe volume 16a located at a desired opto-acoustic remote sensing range A from telescope 74. Particles suspended within probe volume 16a are moving in response to sound waves 20 generated by adverse weather conditions in the atmosphere at a stand off distance B from telescope 74 and light scattered by those particles forms a return beam 76 collected by telescope 74 and collimated by expander 72. Sound arriving in directions close to perpendicular to the remote sensing beam 76 also provide refractive-index coupling. However because of the insensitivity of such coupling relative to particle motion coupling, sound arriving from a forward looking direction provides the dominant form of coupling. Nevertheless the refractive-index coupling could be exploited in order to provide a port/starboard and up/down form of lateral coverage to compliment the longitudinal particle motion coupling within probe volume 16a.

A return beam 76 is then deflected to a Kerr-Cell electro-optic (E-O) transmit/receive (t/r) switch and range gate 80 which is turned on and off by time scale tracker 28. In this way, the time pulsed operation of modulator 24, delay device 48, and gate 80 are all correspondingly controlled by tracker 28, which corrects for instantaneous movement of the aircraft toward probe volume 16a so that the same volume of air is being sensed over a period of time needed to collect multiple laser pulses. Tracker 28 shortens up the pulse rate to driver 26 and gate 80 over time, and signal 50 causes the delay of reference beam 54a to be matched to the changes in the laser pulse go/return time delay incurred during transmission/reception, respectively, through beams 34a and 76 as the aircraft moves towards probe volume 16a and distance A decreases accordingly. The focused telescope will be mounted on a movable platform, such as a gimbled inertial platform, which will be moved in synchronism with tracker 28 to keep the beam pointed at probe volume 16a as the aircraft moves toward the probe volume. The tracker also corrects for laser go/return travel time pulse to pulse variations associated with refractive index changes due to scalar turbulence fluctuations in the immediate atmosphere ahead of the aircraft which changes are caused by temperature, humidity, pressure etc.

Also, without multipulse processing the length of the probe volume and hence the single pulse duration would be constrained by the particle motion (PM) Doppler frequency spreading. Along with single pulse coding applied by the pulse coding driver, a much shorter probe volume also may be accommodated by processing N-pulses.

Return beam 76 leaves range gate 80 to a wavefront curvature divergent optical lens 82 which fans out the return beam into a plurality of beams 84 onto the front face of a 3-D curved off-set axis mirror 86 which reflects each individual beam of the multiple beams 84 onto a pixel on the front face 89 of charge coupled device (CCD) 87.

Reference beam 54a passes through a similar lens 88 which fans the beam into a plurality of reference beams 90 equal in number to beams 84 onto the backside of mirror 86, through the mirror so as to be time and wavelength curvature registered at each associated pixel of CCD 87; wherein it is heterodyne mixed with multiple channel signal information derived from return beam 84. In this way angle-diversity receiving (ADR) is applied to a common probe volume 16a, with each ADR multiple channel "seeing" this volume from a sufficiently different angle so as to average out the "unresolved" components of sonic and subsonic noise appearing as "speckles" across the face of the image plane of the CCD 87. There is an additional plurality of identical processing channels each associated with probe volumes 16b, 16c, etc.

CCD 87 is approximately sized to have 100×100 or $10^4$ pixels on its front face 89, which is consistent with suppressing particle Brownian motion in air and a return beam 84 and a reference beam 90 are optically heterodyne mixed on each pixel. As an alternative to homodyne mixing, which requires four times as many CCD pixels in order to apply spatial filtering for removing the unwanted mixing products, the CCD 87 includes an on-the-chip analog band pass filter 91 and an on-the-chip analog to digital converter 92. The band pass filter accepts the wanted mixing product, i.e., return beam 84×reference beam 90, which contains the instantaneous Doppler information but rejects unwanted mixing products beam 84×beam 84 or beam 90×beam 90. As a result of the time registration provided by path length matching the reference beam 90 with the returned signal beam 84, the coherent optical heterodyne mixing process performed on the face of CCD 87 serves as a replica correlator. The band pass filtering 91 applied to select the beam 84×beam 90 wanted mixing product containing the instantaneous Doppler signal is smoothed in such a way that its averaging action provides pulse compression of the returned coded laser pulse to electronically produce a much more confined range-resolving pulse envelope than the original coded laser pulse. While doing so, it also retains the frequency deviation range of the instantaneous Doppler (i.e. phase rate) modulated signal and noise. This Doppler modulated information is extracted using a phase rate demodulation process comprised of phase demodulation combined with phase unwrapping 96 followed by spatial averaging 98 and digital time differentiation 100 to obtain phase rate information that has benefitted from ADR processing. This wide band phase rate demodulation is more appropriate to this particular function, as opposed to employing the usual bank of Doppler band pass filters, to provide Doppler as well as range information in a replica correlation process. The coded laser pulse compression removes a portion of the previously mentioned constraint in selecting the laser pulse length, thereby "collapsing" the duration of the range gate 80 in order to reject more of the sonic and subsonic noise which, otherwise, would be PM coupled into a much longer equivalent probe volume. The addition of N-pulse processing preserves and extracts the "fine grain" PM Doppler spread information that is impressed in the Doppler "comb"

spectrum region of the digital IQ data stream that is spectrally confined around zero frequency. Application of this N-pulse moving target indicator (MTI) radar type processing allows a single pulse spectrum to become subdivided into an "N-toothed comb", wherein each tooth contains a replica of the PM Doppler frequency spread spectrum. Otherwise in the case of a single wide band pulse the desired Doppler modulation spectrum would be irrevocably smeared by a convolution with the pulse spectrum. Furthermore the frequency band over which "shot" noise would contribute is equally confined. As a consequence of N-pulse processing, the bandwidth of the coded laser pulse may be chosen to provide much shorter radial range resolution probe volume than allowed by single pulse processing. The converter 92 employs quadrature pulse undersampling of the band pass filter to obtain inphase (I) and quadrature (Q) samples on each pixel as a means to apply minimal sample clock-rate requirements for producing a multi-pixel, multi-channel digital I-Q data stream 94. The CCD 87 and its described operation can be conveniently referred to as a CADRE-CORPS (Charge-Coupled Angle Diversity Receiver Extraction by Correlating Optical Replicas for Phase Sensing) Camera.

The multi-channel ADR system provided by CCD 87 substantially reduces "speckle" noise from probe volume 16a and vastly improves the sensitivity of the system over that of a single channel Laser-Doppler velocimeter as depicted for each probe volume shown in the Jacobs' patent. "Speckle" noise results from what is termed a High-Burst Density (HBD) situation. An HBD situation results when photons are returned to an optical receiver from many light-scattering particles populating probe volume 16a at one time. The multiple optical paths over which light may be returned from these multiple particles cause a "speckle" pattern to be distributed across the receiving point on an imaging plane.

The "speckling" arises as a result of constructive and destructive interference between these multiple optical paths. Such "speckles" fluctuate in amplitude as the particles re-arrange themselves within probe volume 16a. Consequently, by viewing the multiple particles within probe volume 16a from a large enough number of obverted angles, consistent with different photodetection points spread as a mosaic across an image plane, so as to sample many statistically independent "speckles", the "speckle" noise may be considerably reduced by combining phase-rate estimates extracted from each CCD. Ideally, the average "speckle" separation distance should match the CCD pixel separations, although minifying optics might have to be accommodated with the optical lens 82 so as to achieve this matching. Apart from this method, when the laser center frequency is shifted (with a sufficient attendant change in light wavelength), the "speckle" pattern changes and becomes less spatially correlated. Therefore, "speckle" noise also may be reduced by combining phase-rate estimates extracted from the probe volume simultaneously illuminated with a large enough number of separate laser-light frequencies. This is the basis for frequency diversity receiver (FDR) processing that may be combined with ADR processing to provide additional "speckle" noise suppression.

The system of the invention embodies a coherent optical receiver to extract phase-rate estimates of the instantaneous Doppler-frequency modulation imparted by particles in motion within and passing through probe volume 16a. The previously mentioned "speckle" noise resulting from amplitude fading manifests itself in one of several ways when coherent processing is employed. This "speckling" reflects changes in particle motion (as well as the refractive-index variations encountered along the optical paths linking through each particle) that varies due to perturbing mechanisms with length scales that are smaller than a characteristic dimension of a probe volume. These motions are said to be "unresolved" by the system. Conversely, motions with length scales larger than a probe volume cause all of the particles within a probe volume to move together without inducing "speckle" fading. Such motions are said to be "resolved" by the system. The "resolved" components contain the sonic field modulations to be recovered for further processing whereas the "unresolved" components represent "speckling" noise. The "resolved" components, in turn, exhibit noise fluctuations around their mean phase-rate variations; one of these mean value quantities time varies directly proportional to the sound-field variations being sensed by the system.

Data stream 94 is fed to a digital phase estimator 96, which incorporates a digital "phase unwrapping", and then through a spatial averager 98 and then to a digital time differentiator 100 for phase rate extraction. The "phase unwrapping" of the phase estimation process 96 is intended to ease the burden placed upon ADR processing. To this end, this invention recognizes the role played when relatively narrow band PM and RI phase-rate modulation noise mechanisms suffer "spectral spreading" as a result of their phase fluctuations passing through some of the regions exhibiting multiple periodic discontinuities characteristic of an arctangent phase-demodulation process. These narrowband PM and RI noise mechanisms, respectively, correspond to such things as velocity and scalar atmospheric turbulence fields. The "phase jumps" caused by the arctangent discontinuities are responsible for the "spikes" resulting in phase-rate demodulation processes as equivalently derived after the digital time differentiator 100.

Prior to the understanding of this action as incorporated into this invention, the consequential "spectral spreading" now known to result from the arctangent discontinuities implicit in phase-rate demodulation was believed to have its root cause in amplitude rather than inphase (I) component fading. As a consequence, this invention separates phase-rate demodulation into phase demodulation with "phase-unwrapping" logic included in the digital time differentiation 100. "Phase unwrapping" may be accomplished by detecting when a discontinuity has been encountered, storing data from around the offending region, then deleting this region, removing the phase jump and smoothing it over. This is done in order to derive "non-spectrally-spread" phase rate estimation from "unwrapped phase" estimation.

Therefore, this form of ADR processing is not burdened with a spatial averaging 98 requirement beyond 100×100= 10,000 multiple channels as needed to suppress the "unresolved" component of atmospheric particle Brownian motion down to its "resolved" component level, that, generally, is forced to be below the "resolved" ambient acoustic noise background level. This requires suppressing 40 dB of unresolved Brownian motion noise, which is consistent with a 100×100=10,000 multiple channel ADR processing. Without "phase unwrapping", the "spectral spreading" of the unresolved components of velocity and scalar (i.e. temperature and specific humidity) fluctuations due to atmospheric turbulence would necessitate using an ADR having about 10,000×10,000=1,000,000 multiple channels to provide approximately 60 dB of "unresolved" noise supression.

A data stream signal 102a from differentiator 100 contains digital information about the conditions of phase-rate modulations arising from probe volume 16a. Similarly, a data stream 102b, 102c, etc. is produced for each volume 16b, 16c, etc. Those data streams are fed into a time domain digital beam forming device 104 that zooms to focus onto a predetermined accoustic range. This device produces a plurality of multiple channel beams 106, e.g. 128 in number, generally designed to correspond to the number of probe volumes 16a, 16b, etc., with beams 106 being distributed over azimuth and elevation depression angle. In addition, the acoustic range focussing may be caused to scan over the whole radial-range scale in a "time-lapse" fashion for display 112 purposes. Beams 106 go to a processor 108 which processes the beam information to simultaneously derive accurate three-dimensional detection, classification, localization and tracking of the hazardous weather conditions at stand-off distance B. Processed beams 110 are then transmitted to a pilot visible display panel 112 which may indicate sonic-contact intensity in color coded form displayed against various 2-dimensional contour plots involving pair wise combinations of the azimuth, and elevation/depression angles as well as range of the hazardous weather conditions stabilized with respect to the aircraft. In addition, a 3-dimensional color display may be formed showing a "look ahead view" of information presented against azimuth and elevation/depression angles, with a "time-lapsed" scan of this picture slowly zoomed through the whole radial range scale to depict scene changes in the third range-dependent dimension. Such a display could be frozen on a particular radial-range focal region by user selection.

While the PM-coupled system 10 has been thus far described and illustrated for use directly on the front of an aircraft, a somewhat simpler version of the system may also be mounted on the ground at the end of an airport runway with the laser beams projecting along the approach path to the runway. A ground based system would not need the pulse tracking and beam stabilization functions since the system is fixed in the ground rather than on a moving aircraft.

Figures 4, 5:
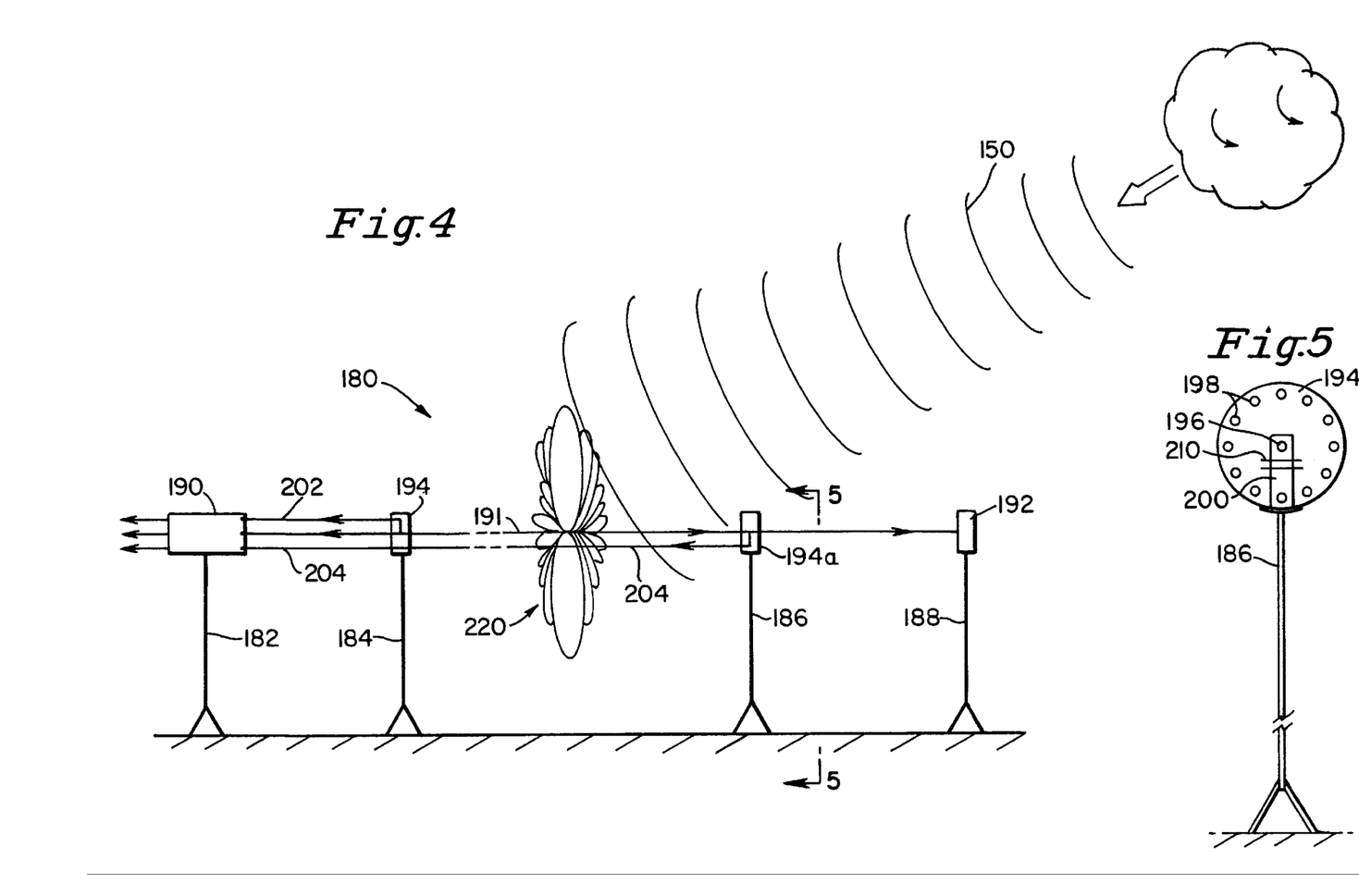
FIG. 4 is a schematic of a ground based embodiment of the laser system of the invention which measures change in the travel time of a light beam caused by a change in the refractive index of the atmosphere caused by sound waves produced by hazardous weather and wake vortex conditions.
FIG. 5 is a view taken along line 5—5 of FIG. 4.

The embodiment of the SOCRATES invention illustrated in FIGS. 4 and 5 shows a ground based system 180 adapted to extend across an airport runway 128 or, in another case, offset to be parallel to an airport runway and utilizing refractive index (RI) coupling responsive to sound waves 150 produced by various aviation atmospheric hazards. System 180 employs a segmented optical line array using retroreflectors (SOLAR) approach and includes a plurality of adjustable leveling tripods 182, 184, 186 and 188 spaced uniformly and in line across runway 128 or placed in an offset position parallel to runway 128. A dual axis pair of such systems, called binary segmented optical line arrays using retroreflectors (BINARY SOLARs) may be oriented at right angles to each other. In this way, the overlapping regions formed by pairs of dual axis multiple or steerable beams may be utilized to provide the system additional localization capabilities.

Mounted on tripod 182 is a combination laser transmitter and coherent optical receiver module 190 which transmits a laser beam 191 to an aligned cooperative fully reflecting external optical corner reflector 192 mounted on right end tripod 188. On each of the intermediate tripods 184 an 186 are identical partially reflecting retroreflectors 194 and 194a each of which will reflect part of beam 191 back to transmitter-receiver 190. As shown in FIG. 5 each retroreflector 194, 194a, etc. includes a center hole 196 which allows the transmitter beam 191 to reach corner reflector 192 and return back to transmitter-receiver 190. Retroreflector also includes a plurality of circumferential equiangularly spaced light holes 198 and a rotatable light deflection arm 200 using a partially and fully reflecting mirror to reflect part of transmit beam 191 back through a selected one of holes 198 to transmitter-receiver 190. For example, in retroreflector 192 arm 200 is aligned with one of holes 198 to provide a return beam 202 at one radial position with respect to receiver 190. In retroreflector 194a arm 200 will be aligned with another hole 198 radially offset from that of retroreflector 194 to provide a return beam 204 which is angularly offset from and does not interfere with return beam 202.

The number of intermediate pedestals 184, 186, etc. and the associated number of partial retroreflectors 194, 194a, 194b, etc. may be as high as 32 so as to provide 32 circumferentially equi-angularly spaced return optical beams 202, 204, etc. back to circumferentially spaced photodetectors 204 on transmitter-receiver 190 in such a way that each return optical beam does not interfere with the other partially retroreflective optical beams. The return beam from the 100% corner reflective 192 returns along the center optical path through the aligned center holes 196 of retroreflectors 194, 194a, 194b, etc. on arm 200 on each of the retroreflectors 194, 194a, etc. A selected number of cascaded neutral density optical filters 210 may be provided to adjust and equalize the attenuation of the respective optical path.

Accurate alignment of corner reflector 192 and retroreflectors 194, 194a, etc. could be accomplished by using a surveyor's lidar or an optical radar target localizer instrument to thread the return optical light beams through their respective positions as defined by the radial position of its respective arm 200 and selected hole 198. A surveyor's lidar or optical radar target localizer has a course aligning telescope and a pulse laser finely aligned narrow beam and range gated receiver capability. A surveyor first locates pedestal 188 and corner reflector 192 in its desired position and then sequentially from right to left as shown in FIG. 4 would adjust each of the intermediate pedestals 186, 184, etc. and retroreflectors 194a, 194, etc, so that the center holes 196 and circumferential holes 198 of all of the retroreflectors are in proper alignment. Pedestal 182 is then properly adjusted to position transmit receiver module 190 so that beam 191 would be accurately aligned with center holes 196 and corner reflector 192. The light deflecting arm 200 of each retroreflector is then properly rotated to a selected angular position so that a return beam from each retroreflector 194 does not interfere with the radially offset return beams from the other retroreflectors 194, 194a, 194b, etc.

The SOLAR system 180 provides an optical line array from which accoustic multi-beam or beam steerable response patterns 220 may be formed. Such beam formed pattern responses are capable of receiving and localizing distant sound sources 150 and rejecting local sonic and subsonic interference. A closely spaced parallel back-to-back arrangement of a pair of SOLAR systems, called twin segmented optical line arrays using retroreflectors (TWIN SOLARs), may be provided. This arrangement could be phased so as to accept sonic energy from the runway approach corridor while rejecting back-lobe sonic energy arriving from the aircraft engines, particularly during the application of the engine thrust reversers after the plane has touched down on the runway.

Each light deflecting arm 200 of retroreflector 194 is fed by a partially reflecting mirror that allows a predetermined portion of the transmit beam 191 to continue along an undisturbed "spool center line" path along the arm to an aligned selected hole 198 by which that light portion is returned to transmit receiver 190. A proper set of neutral density optical filters 210 are selectively switched into the radial light beam path along arm 200 to thereby step quantisize the respective amount of optical attenuation required for a particular retroreflector 194. This is done so that each of the partially reflecting retroreflectors 194, 194*a*, etc. is adjustable so as to return the same average number of photons as returned by the fully reflecting corner reflector 192. Arm 200 of a particular retroreflector 194 may be clicked into and radially located in a selected hole 198 so that that particular retroreflector is preset to provide mutually exclusive offset-deflected return light beam having a preselected optical attenuation matching the particular optical retroreflector's position within the optical line array. Each return light beam would be radially aligned to pass unimpeded through the unoccupied circumferential holes 198 of the retroreflectors 194, 194*a*, etc. between it and its individual optical receiving photodetector 204, a plurality of which are circumferentially arranged on a circular optical receiving plane of transmiter-receiver 190.

The described SOLAR system enables the formation of multiple fixed or steerable beams and the application of optimum or adaptively controlled complex weights to segments. This is performed by applying certain vector-matrix manipulations of an assemblage of optical returns from all of the retroreflectors for the purpose of controlling beam nulls or performing sonic or subsonic noise cancellation.

The individual travel times along the laser beams and return beams are varied in concert with the compressions and rarefactions of an incident sound wave 150 generated by hazardous aviation conditions in the atmosphere such as wake vortices, downdrafts, updrafts, etc., with the change in the respective variations of the refractive index of each of the beams providing the travel time changes which serve as an indication of arrival direction of sonic emissions from those hazardous conditions. These travel time changes also follow the time waveform excursions of the incident sound wave and serve to characterize the source mechanics creating the sound.

In an RI coupling system which would simply employ a transmit receiver such as module 190 and the corner reflector 192 to produce a single go-return optical beam, the resulting sound response pattern has a sine x/x characteristic with its maximum response axis (MRA) normal to the bisector of a bistatic angle or the common axis of a monostatic angle system and is axially symmetrically disposed around it. This single go-return optical beam system has the disadvantage that the sound response pattern of this optical line array can not be beamsteered to move its MRA away from a position normal to the bisector or common axis of the go-return beam. In contrast, the described SOLAR system 180 overcomes this disadvantage by providing multiple fixed or steerable beams.

In populating the optical line array for unambiguous beamforming/beamsteering up to a given frequency at the top of a frequency band of interest, a one half acoustic wavelength or less spacing (determined by the band top frequency) is necessary when beamsteering away from a broadside direction. This is needed in order to avoid ambiguous grating lobes that eventually result in rabbit-ears beam splitting and, then, more complicated rose-petal patterns as the spacing increases beyond an acoustic wavelength.

For broadside-direction beamsteering, the broadside beam width is given approximately by the reciprocal of the number of acoustic wavelengths distributed along the external go-return optical beam pathlength. As an endfire beamsteering direction is approached, because of an aperture foreshortening effect, the acoustic beam response broadens. In addition, without reducing the spacing to one-quarter of an acoustic wavelength, endfire beams with their MRAs pointing equally in both endfire directions are formed. With one-quarter acoustic wavelength spacing, this suggests the need for at least 16 or preferably 32 pedestals and partial reflecting retroreflectors, plus the external 100% reflecting retroreflector. Each of these retroreflectors would be a passive optical device.

The beamforming for a SOLAR approach could be quite complicated because each segment is nested and therefore partially overlaps the next longer one and those beyond it. This is because the acoustic response pattern associated with a particular partially reflecting retroreflector is determined by the one-way optical pathlength between the generally collated laser transmitter/coherent optical receiver and this retroreflector. From an entirely acoustic response viewpoint, conventional segmented-sensor acoustic responses may be derived by subtracting the phase rate modulation (PRM) of one origin-to-retroreflector segment from that of the adjacent overlapping origin-to-retroreflector segment. Complex weights may be derived to weight these different PRM components to optionally extract sonic signals from sonic noise as it were, placing nulls on discretely located sonic noise sources. However, it has been shown that, when subsonic noise sources dominate, this arrangement does not result in the best preferential gain in terms of suppressing subsonic noise more than sonic noise. When optimum complex weights are to be applied to the overlapped segment PRM components in the case where subsonic noise dominates, these complex weights have magnitudes proportional to the length of each nested overlapped segment.

Regardless of these beamforming complications, suitable beamshaping, pointing, sidelobe control and null control can be accomplished. Moreover, multiple SOLAR or BINARY SOLAR or TWIN SOLAR segmented optical line arrays may be arranged to form a 2-D or even 3-D array configuration. Then, by employing suitable phases (as a function of frequency) or time delays, respectively, frequency or time-domain beamforming, including real or complex weights for sidelobe or null control may be affected to provide further beam sharpening.

Figures 6, 6A, 6B:
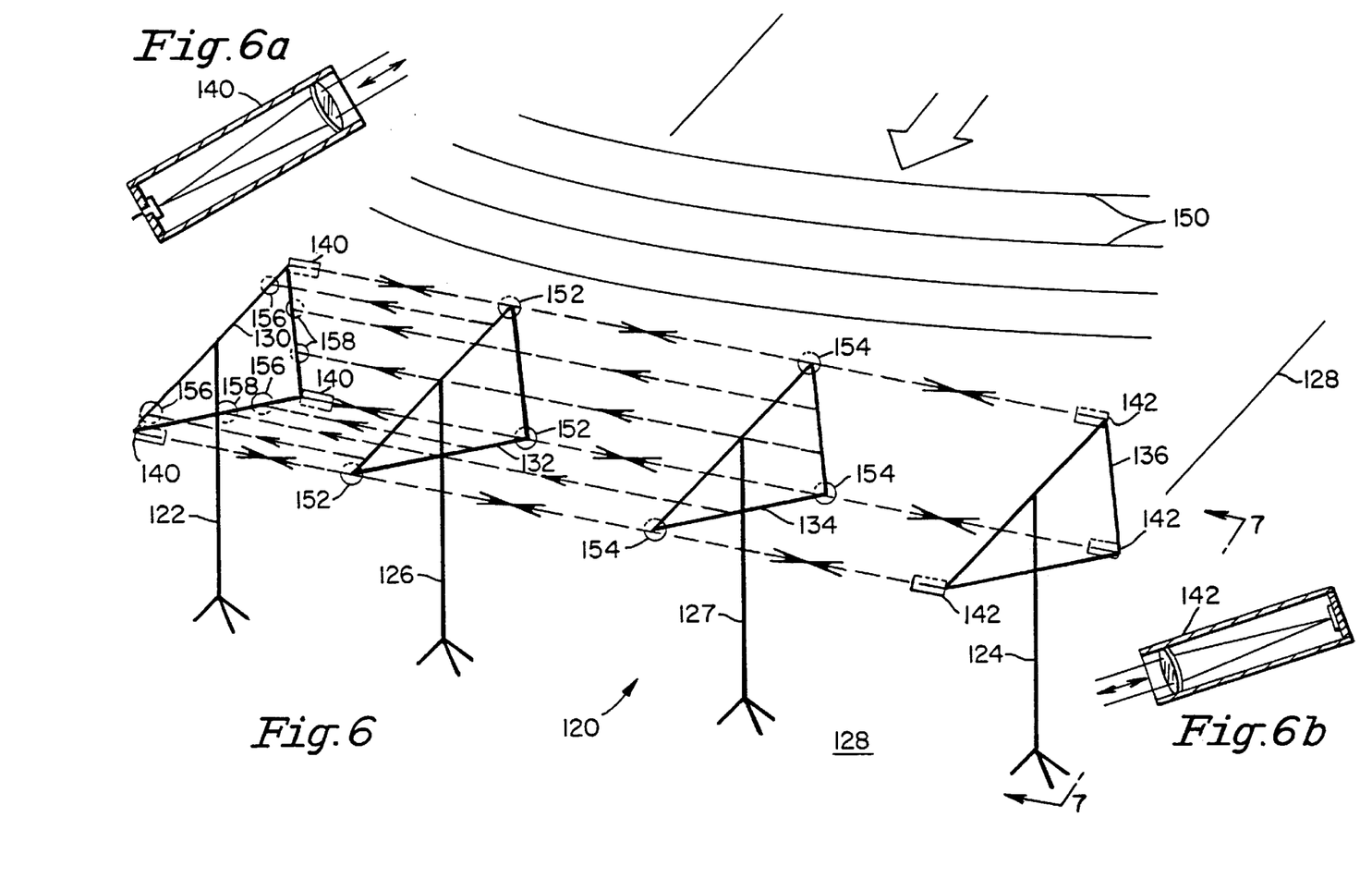
FIG. 6 is a second embodiment of a ground based system responding to change in the travel time of a light beam.
FIG. 6a is an enlarged view of the transmit/receive module incorporated in the ground base system of FIG. 6.
FIG. 6b is an enlarged view of a fully reflective corner retroreflector which is part of the ground base system of FIG. 6.
Figure 7:
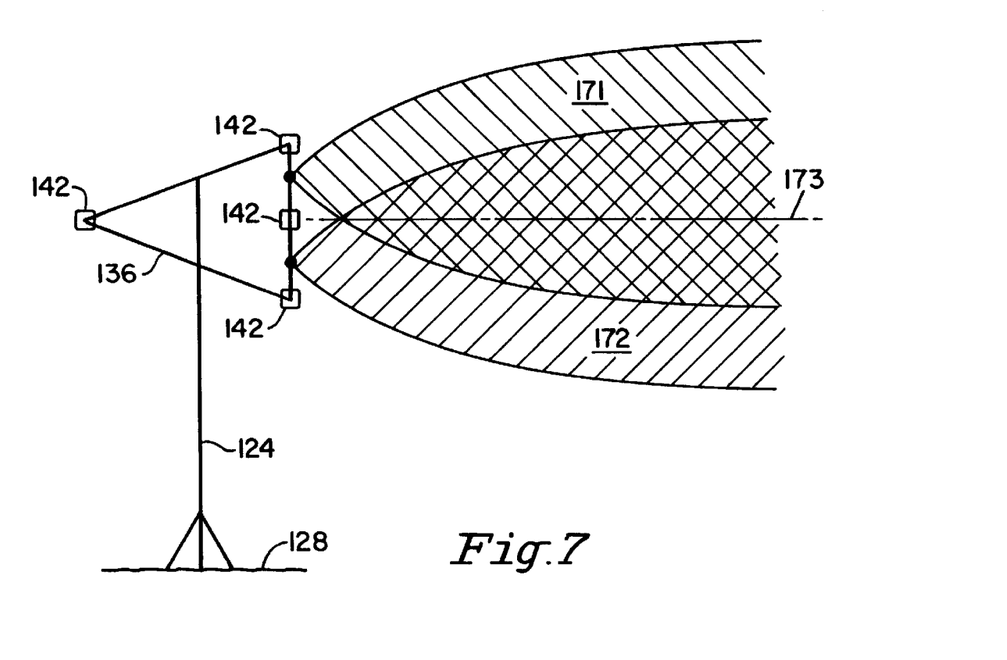
FIG. 7 is a view taken along line 7—7 of FIG. 6.

Another embodiment of the invention is shown in FIGS. 6 and 7 and illustrates a simplified ground based system 120 adapted to extend across an airport runway 128 and also utilizing refractive index (RI) coupling responsive to sound waves 150 produced by various aviation atmospheric hazards.

System 120 includes left and right end pedestals 122 and 124 and a pair of intermediate pedestals 126, 127 laterally spaced across the "undershoot" approach corridor to an airport runway 128 with each supporting a triangular rod frame 130, 132, 134 and 136, the corners of the frames being aligned with each other and adjacent frames establishing three segments therebetween.

At each corner of left end frame 130 is a combination transmit/receive module 140 which transmits a laser beam to an aligned fully reflective corner retroreflector 142 on frame 136 and also receives the reflected return beam from the retroreflector. Using an optical beam splitter along with optical fibers, optical power from a sufficiently powerful CW laser may be shared between all three transmit locations 140 on the corner of frame 130. Thus, three horizontally and vertically spaced sensing beams or modes are provided in the system between aligned corners of the frames. The individual travel times along these laser beams are varied in concert with the compressions and rarefactions of an incident sound wave 150 generated by hazardous aviation conditions in the atmosphere such as wake vortices, downdrafts, updrafts, etc., with the change in the respective variations of the refractive index of each of the beams providing the travel time changes which serve as an indication of arrival direction of those hazardous conditions. These travel time changes also follow the time waveform excursions of the incident sound wave and serve to characterize the source mechanics creating this sound.

To provide horizontal localization accuracy, the basic form of this other embodiment employs partial retroreflectors 152 that are mounted at each corner of frame 132 and partial retroreflectors 154 that are mounted at each corner of frame 134. Retroreflectors 152 and 154 are the same as retroreflectors 194 of FIG. 5, and are aligned in order to allow the transmitter beam from each of the three modules 140 to reach and return from corner reflector 142 mounted on the corners of frame 136. Parts of the beams transmitted from modules 140 will be reflected by partial retroreflectors 152 back to photodetectors 156 on frame 130. Similarly, parts of the beams from modules 140 will be reflected by partial retroreflectors 154 to photodetectors 158 on frame 130. The light deflection arms 196 of aligned retroreflectors 152 and 154 are radially positioned so that the return beams from those retroreflectors are radially offset and do not interfere with each other. The remaining major portion of the laser beams from modules 140 pass on to "cats-eye" retroreflectors 142 from where they are reflected back to modules 140. Thus, each beam clustered mode has a set of three photodetectors on frame 130 associated therewith. The change in the refractive index of the light beams as sensed by the photodetectors is then suitably processed to provide early warning information to ground personnel.

As described this other embodiment of the SOLAR approach is able to passively localize the azimuthal arrival angle and the radial range from whence the acoustic wavefront 150 is emanating. It does this using time-delay estimates of the differences in time of arrival of sonic energy arriving at the phase centers between the subapertures confined between the transmit/receive modules located at the top and the bottom of the front face of frame 130 and the corresponding partial retroreflectors 152 located at the top and the bottom of the front face of frame 132 for the left subaperture, similarly for frame 134 for the center subaperture, and from the "cats-eye" retroreflector 142 for the right subaperture. In that these three subapertures partially overlap each other, three distinctly separated but continuous subaperture responses are crated by differencing the adjacent subaperture RI-coupled signal responses as also described for SOLAR processing. This other embodiment may be substituted using the pedestals to estimate wavefront horizontal tilt and curvature, respectively, to determine azimuth angle and radial range in lieu of the SOLAR beamforming or beamsteering function allowed by segmenting the overall aperture.

As described, the FIG. 6 configuration of this other embodiment of SOLAR only facilitates estimating elevation/depression angles from the rather broad vertical acoustic response pattern determined by the common vertical dimensions of the left, middle and right subapertures. To increase the accuracy of this system, a similar combination of transmit/receive module 140 and "cats eye" retroreflector 142 along with intermediate partial retroreflectors 152 and 154 respectively combined with their corresponding photodetectors 156 and 158, is inserted at the center of the front faces of the respective frames 130, 136, 132 and 134. The various optical beam paths running between the vertical centers of the left, middle and right subapertures parallel similar optical beam paths provided at the rear apex of frames 130, 136, 132 and 134. However, subaperture signals derived from these rear apex optical beam paths are used in concert with the corresponding front-face optical beam paths in order to cancel out a back-lobe sonic response of each subaperture.

FIG. 7 shows this cluster mode of front-face centered optical beam paths by designating an additional 142 location looking into the right frame 136 mounted on pedestal 124. In this way, each horizontally displaced subaperture is further subdivided into an upper and a lower subaperture. The frame 136 and its corresponding frames all may be vertically tilted through common angle in order to compensate for the illusion of vertical beam tilt brought about by a low grazing angle beam null resulting from interference with a 180° phase-shifted ground-plane 128 reflected sonic wave that cancels the direct sonic wave 150. Each tip and down subaperture produces an overlapping up and down 172 vertical beam response. Within this vertical beam overlapping angular region, time-delay differences between their vertical phase centers may be estimated. In this way, the introduction of this additional cluster mode shown in FIG. 7 serves to improve the vertical angle estimation accuracy by estimating elevation/depression angles around the beam cross-over axis 173 from these time-delay differences that relate to vertical wavefront tilt.

Without the overlapping acoustic vertical sensing beams 171 and 172 across the front of frames 130, 132, 134 and 136, system 120 only would provide limited vertical angle estimation accuracy along with back-to-front beam response suppression for sensing the sound waves 150 moving towards the frames. As stated, the frames may be tilted slightly upward to minimize interaction with the ground under the approach corridor 128. In addition, overlapping acoustic vertical sensing beams 171 and 172 result from a similar combination of a transmitter/receiver module 140 with a corner reflector 142, and suitably optical beam offsetting partial retroreflectors 152 and 154, along with corresponding offset photodetectors that may be jointly introduced respectively centered on the front face of frames 130, 132, 134 and 136. As stated, this additional beam cluster mode facilitates better vertical angle estimation accuracy by virtue of split beam processing of upper and lower acoustic receiving beams 171, 172 disposed around their cross-over axis 173. The system may be called a SOLAR-ECLIPSE system, i.e., it is a segmented optical line array using retroreflectors and provides elevation and curvature localization for inferring the position of sonic emanations. It processes wavefront horizontal and vertical tilt of an incident acoustic wave to obtain azimuth and elevation angle estimates with wavefront curvature passively indicating range.

While the RI coupling systems illustrated in FIGS. 4 and 5 and FIGS. 6 and 7 have been described for particular use as ground base systems, they may also be employed in airborne configurations, for example from tip to tip of the wings, port wing tip to port fuselage-starboard fuselage to starboard wing tip, or a light beam connecting between an upper fuselage point, say, behind the cockpit to the upper tip of the aircraft vertical stabilizer. The former RI-coupling configuration provides coverage directly ahead or behind the aircraft, whereas the latter configuration provides RI-coupling of acoustic signals arriving from port or starboard directions of the aircraft. While each of these approaches may be suitable for some applications, the particle motion coupling system illustrated in FIGS. 1–3 remains the preferred airborne system.

Another modified embodiment may include the use of fiber optic cable configured as optical wave guides which respond to sound induced strain along the length of the fiber, with corresponding fiber cross sectional changes both resulting in fiber refractive index changes. This includes any method for employing electro-optic or other techniques to form optical coded pulses that could be returned to an optical or photodetector coherent heterodyne or homodyne receiver, for example, through Rayleigh or Mie optical leakscattering from random or deterministically distributed occlusions contained through the fiber. Such methods, most likely would use pulse decoding to collapse the optical pulses along with electro-optic or electronic range gating as a means to delineate individual extended microphone sensor segments. In a fashion similar to using free optical waves in a SOLAR system approach, any of these optical waveguide methods could contigously place such extended microphone sensors throughout an acoustic sonic aperture. As with the optical beams in the embodiments of FIGS. 1–7 the refractive index changes in the optical fiber wave guides caused by radiated sound may be indicative of hazardous atmospheric conditions generating that sound.

Another modification may include accoustic microphones mounted on the leading edge of each wing of an aircraft or across or offset and parallel to the runway to detect soundwaves generated by hazardous weather conditions and/or wake vortices.

Further the embodiment illustrated in FIG. 3 may be modified by substituting an all optical form of the system described herein called PHARAOH (phase rate assessment by optical holography), which is an all optical multi-channel angle diversity receiver (ADR) that uses photons instead of electrons to perform operations similar to the coherent optical CCD-based camera described above with respect to FIG. 3. The PHARAOH type of ADR processing would not require a CCD, using instead optical degenerate two-wave mixing (DTWM) creating a coherent optical heterodyne form of an orthogonal pair light-carrier borne components, thereby providing a function similar to an electronically derived I&Q components.

Also in the embodiment of FIG. 3, the angle diversity receiver may be replaced by a frequency diversity receiver (FDR) for "unresolved" noise suppression. Also as an adjunct to the pulse tracker 28 in FIG. 3, a wave vector frequency filtering (WVFF) system may be provided to remove the "signal" masking effect associated with platform motion causing spectrum stretching into the signal frequency band of the "resolved" subsonic noise components. An alternative to wave vector frequency filtering involves signal free reference (SFR) adaptive noise cancellation technique that can be applied using either coherent optical homodyne or heterodyne processing for "resolved" subsonic noise cancellation. All of these embodiments may be integrated into the CADRE-CORPS or PHARAOH camera.

Other embodiments of the invention include using a nonlinearly generated and radial range focused acoustic sawtooth wave to create an acouso-optic mirror (AOM) acting as a retroreflector. Sufficient acoustic enhancement to create a shock front to a nonlinear acoustic sawtooth wave is brought about by transmitting a synthetic spectrum waveform using a multiple set of phase locked, pulsed acoustic carrier waveforms each emitted from individual projectors in a large array of loudspeakers. Constructive interference occurs when these acoustic pulses come together to add coherently in a predetermined focal region. The resultant acoustic peak-pressure enhancement results in very sharp fronted pressure discontinuities being periodically formed through nonlinear acoustic interaction.

The periodically spaced, very sharp nonlinear shock fronts are attended by equally sharp optical refractive-index (RI) discontinuities. Each of these discontinuities act as optical mirror and, when the acoustical wavelength is adjusted to be a multiple of half an optical wavelength, Bragg scattering enhances the returned optical field strength. Further enhancement may be achieved using a form of reseeded Brillouin scattering (RBS) employing a technique called optical phase conjugation (OPC). Traditionally RBS has been used to achieve a one-hundred fold reduction in the Doppler-frequency spreading associated with spontaneous Brillouin scattering that, at a relatively low level of optical radiance causes the photons to spontaneously create isentopic fluctuations corresponding to broadly propagating and evanescent phonons. At a higher level of radiance, stimulated Brillouin scattering (SBS) occurs wherein the phonon directionality becomes much more orderly and, thereby, reduces the Doppler-frequency spreading created through "phonon motion" by one-order-of magnitude relative to spontaneous Brillouin scattering.

SBS has been used with gases confined within an optical waveguiding tube to create an OPC mirror so distorted as to remove optical wavefront distortions and, unlike conventional mirrors, cause the impinging light to retrace the original path it took prior to reflection. Other photorefractive materials, such as lead titanate, may be made to produce a slowly forming corrective OPC mirror at lower radiance levels than required by SBS. This is accomplished by a process called degenerate four-wave mixing (DFWM). It is noted that a degenerate two-wave mixing (DTWM) form of this process was mentioned in the context of nonlinear optical processing applicable to PHARAOH.

RBS can use quite high optical radiance levels that can be brought about through the correction of atmospheric optical aberration using OPC so that phonons are directly created by highly concentrated light. When used in combination with the AOM, the RBS process employs a FWDM approach to "reseed" the laser light scattered from nonlinear acoustically generated phonons. The combination of these two processes is intended to sharpen the optical RI discontinuity in a way that serves to reduce the mirror reflection losses attending an otherwise normal shock front thickness that, without RBS enhancement, would not be a sufficiently small fraction of an optical wavelength. When combined with period nonlinear acoustic wave Bragg scattering, the RBS enhanced AOM offers an efficient "sky hook" mirror thereby supplanting the need to confine RI coupling for airborne application to where retroreflectors may be accommodated within the constraints of aircraft wing span fuselage dimensions.

Another possibility could be to employ an acoustic-electromagnetic approach wherein electromagnetic energy would be propagated either as free or waveguided radio waves, instead of optical waves, in response to sound generated by atmospheric hazards. For example, a system identified as an extended radio acoustic sounding system (ERASS) employing a focused non-linear acoustic wave set, along with Bragg scattering as described in the AOM above, but utilizing radio waves instead of optical waves may be used to interrogate a progressive acoustic field created by aviation atmospheric hazards.

A further embodiment may include the use of waveguided radio waves, using coaxial cable, to interrogate sound fields through Bragg backscattering.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

I claim:

1. A method of detecting adverse weather conditions in the atmosphere which pose a hazard to flying aircraft, the adverse conditions producing sound waves in the atmosphere, comprising providing a laser device which produces an optical beam, directing the optical beam into a probe volume of the atmosphere containing light reflecting matter which moves in response to said sound waves, collecting the light reflected from said matter, and producing output information from said collected light indicative of said sound waves and the weather conditions of the atmosphere.

2. The method of claim 1, wherein the adverse weather conditions are present in a region of the atmosphere which is spaced a substantial distance from the probe volume.

3. The method of claim 1, wherein the reflected light is collected by a multi-channel receiver which senses random movement of individual particles of light reflecting matter within said probe volume.

4. The method of claim 1, wherein the laser device is mounted at the front of the aircraft and the probe volume is ahead of the aircraft along its flight path.

5. The method of claim 1, wherein the laser device is mounted adjacent a runway for an aircraft.

6. A method of detecting adverse weather conditions in the atmosphere which pose a hazard to flying aircraft, the adverse weather conditions producing sound waves in the atmosphere, comprising producing a plurality of optical beams, directing each optical beam into an associated probe volume of the atmosphere containing light reflecting matter which moves in response to said sound waves, collecting the light reflected from said matter in each probe volume, producing a signal from the collected light from each probe volume, combining said signals to produce output information indicative of the characteristics and locations of said sound waves and the weather conditions of the atmosphere.

7. The method of claim 6, wherein the adverse weather conditions are present in a region of the atmosphere which is spaced a substantial distance from the probe volumes.

8. The method of claim 6, wherein the reflected light from each probe volume is collected by a multi-channel receiver which senses random movement of individual particles of light reflecting matter within each said probe volume.

9. The method of claim 6, wherein the optical beams are produced by laser means mounted at the front of the aircraft and the probe volumes are located ahead of the aircraft along its flight path.

10. The method of claim 9, wherein the probe volumes are arranged in a three dimensional substantially truncated conical configuration and act as virtual microphones.

11. A method of detecting conditions in the atmosphere which are hazardous to flying aircraft, said hazardous conditions producing sound waves in the atmosphere, comprising providing a laser device which produces an optical beam, directing said beam into the atmosphere and measuring the effect of said sound waves on said beam as an indicator of said hazardous conditions.

12. The method of claim 11, wherein said laser device is mounted on the front of an aircraft.

13. The method of claim 11, wherein said laser device is mounted adjacent a runway for an aircraft.

14. The method of claim 13, wherein a plurality of horizontally and vertically spaced optical beams are directed across the runway and reflected back to photodetectors and measuring the change in travel time of said beams as an indicator of said hazardous conditions.

15. The method of claim 14, wherein portions of said beams are reflected back to photodetectors at selected distances across said runway.

16. The method of claim 13, wherein said beam is directed across said runway, reflecting a segment of said beam at each of a plurality of locations laterally spaced across said runway to provide a plurality of return beams reflected back to photodetectors, and measuring the change in travel time of said beams as an indicator of said hazardous conditions.

17. The method of claim 16, wherein said return beams are circumferentially angularly spaced from each other so as not to interfere with each other.

18. The method of claim 11, wherein said beam extends from a first location to a second location on an aircraft, reflecting a segment of said beam at each of a plurality of locations laterally spaced between said first and second locations to provide a plurality of return beams back to photodetectors, and measuring the change in travel time of said beams as an indicator of said hazardous conditions.

19. The method of claim 18, wherein said return beams are circumferentially angularly spaced from each other so as not to interfere with each other.

20. The method of claim 11, wherein said beam is guided by fiber optic cable means.

21. Apparatus for detecting conditions in the atmosphere which are hazardous to flying aircraft, said hazardous conditions producing sound waves in the atmosphere, comprising laser means for producing an optical beam, means for directing said beam into the atmosphere, and means for measuring the effect of said sound waves on said beam as an indicator of said hazardous conditions.

22. The apparatus of claim 21, wherein said laser means is mounted on an aircraft.

23. The apparatus of claim 21, wherein said laser means is mounted adjacent a runway for an aircraft.

24. The apparatus of claim 23, wherein said laser means produces a plurality of horizontally and vertically spaced optical beams which are directed across the runway, means for reflecting said beams back to photodetectors, and means for measuring the change in travel time of said beams as an indicator of said hazardous conditions.

25. The apparatus of claim 24, comprising means for reflecting portions of said beams back to photodetectors at selected distances across said runway.

26. The apparatus of claim 23, comprising means for directing said beam across said runway, means for reflecting a segment of said beam at each of a plurality of locations laterally spaced across said runway to provide a plurality of return beams reflected back to photodetectors, and means for measuring the change in travel time of said beams as an indicator of said hazardous conditions.

27. The apparatus of claim 26, comprising means for circumferentially spacing said return beams from each other so as not to interfere with each other.

28. The apparatus of claim 21, said directing means including fiber optic cable means for guiding said beam.

29. Apparatus for detecting adverse weather conditions in the atmosphere which pose a hazard to flying aircraft, the adverse conditions producing sound waves in the atmosphere, comprising laser means for producing an optical beam, means for directing the optical beam into a probe volume of the atmosphere containing light reflecting matter which moves in response to said sound waves, means for collecting the light reflected from said matter, and means for producing output information from said collected light indicative of said sound waves and the weather conditions of the atmosphere.

30. The apparatus of claim 29, wherein the adverse weather conditions are present in a region of the atmosphere which is spaced a substantial distance from the probe volume.

31. The apparatus of claim 29, wherein said collecting means includes a multi-channel receiver which senses random movement of individual particles of light reflecting matter within said probe volume.

32. The apparatus of claim 29, comprising means for mounting said laser means at the front of the aircraft and the probe volume is ahead of the aircraft along its flight path.

33. The apparatus of claim 29, comprising means for mounting said laser means adjacent a runway for an aircraft.

* * * * *